United States Patent
Wang

(10) Patent No.: US 10,467,738 B2
(45) Date of Patent: Nov. 5, 2019

(54) DISPLAY GRAY SCALE CURVE CORRECTION SYSTEM AND METHOD FOR MOLYBDENUM TARGET MAMMOGRAPHY

(71) Applicant: Nanjing Jusha Display Technology Co., Ltd., Nanjing (CN)

(72) Inventor: Wei Wang, Nanjing (CN)

(73) Assignee: Nanjing Jusha Display Technology Co., Ltd., Nanjing (CN)

( * ) Notice: Subject to any disclaimer, the term of this patent is extended or adjusted under 35 U.S.C. 154(b) by 0 days.

(21) Appl. No.: 15/763,693

(22) PCT Filed: Oct. 20, 2015

(86) PCT No.: PCT/CN2015/092253
§ 371 (c)(1),
(2) Date: Mar. 27, 2018

(87) PCT Pub. No.: WO2017/059605
PCT Pub. Date: Apr. 13, 2017

(65) Prior Publication Data
US 2018/0286025 A1    Oct. 4, 2018

(30) Foreign Application Priority Data
Oct. 7, 2015    (CN) .......... 2015 1 06376412

(51) Int. Cl.
*G06T 5/40* (2006.01)
*A61B 6/00* (2006.01)
(Continued)

(52) U.S. Cl.
CPC ............... *G06T 5/40* (2013.01); *A61B 6/463* (2013.01); *A61B 6/502* (2013.01);
(Continued)

(58) Field of Classification Search
CPC ........ G09G 5/10; G09G 2380/08; G06T 5/40; G06T 5/009; G06T 7/0012;
(Continued)

(56) References Cited

U.S. PATENT DOCUMENTS

2009/0252396 A1    10/2009  Morita
2016/0078825 A1*   3/2016   Kim ..................... G09G 3/3607
                                                   345/89

FOREIGN PATENT DOCUMENTS

CN    101393010 A  *  3/2009
CN    101393010 A     3/2009
(Continued)

OTHER PUBLICATIONS

Michael Flynn; Image Presentation: Implications of Processing and Display; Mar. 12, 2008; CDC; Retrieved from the Internet on Apr. 28, 2019: https://www.cdc.gov/niosh/docs/2008-139/pdfs/Pres-Flynn-ProcessingDisplay.pdf?id=10.26616/NIOSHPUB2008139 (Year: 2008).*

(Continued)

*Primary Examiner* — Michael Le
(74) *Attorney, Agent, or Firm* — Kramer Levin Naftalis & Frankel LLP

(57) ABSTRACT

The present invention discloses a display gray scale curve correction system and method for molybdenum target mammography, comprising: a key module, an ARM module, an upper computer, an FPGA module connected with the outputs of the ARM module and the upper computer, and a display panel connected with the output of the FPGA module, wherein the upper computer firstly captures the currently displayed mammography, then analyzes the image features, calculates the optimized gray scale correction curve, and the ARM module writes the gray scale correction curve into the FPGA module through a serial communication protocol; the FPGA module performs grayscale map- (Continued)

ping twice for pixel values of the input image, and enhances the display of the mammography image. Compared with the standard DICOM calibration curve, the features of the mammography X-ray image are included in the scope of the optimization, which can highlight the possible parts of the lesion. Furthermore, the present invention is convenient to operate and does not occupy the upper computer resources to ensure smooth operation.

6 Claims, 3 Drawing Sheets

(51) Int. Cl.
 *G06F 13/42* (2006.01)
 *G06K 9/46* (2006.01)
 *G06T 7/00* (2017.01)
 *G09G 5/10* (2006.01)

(52) U.S. Cl.
 CPC ....... *G06F 13/4282* (2013.01); *G06K 9/4647* (2013.01); *G06T 7/0012* (2013.01); *G09G 5/10* (2013.01); *G06F 2213/0016* (2013.01); *G06T 2207/10116* (2013.01); *G06T 2207/30068* (2013.01); *G09G 2380/08* (2013.01)

(58) Field of Classification Search
 CPC . G06T 2207/10116; G06T 2207/30068; A61B 6/463; A61B 6/502; G06K 9/4647; G06F 13/4282; G06F 2213/0016
 See application file for complete search history.

(56) References Cited

FOREIGN PATENT DOCUMENTS

| | | | |
|---|---|---|---|
| CN | 101477683 A | * | 7/2009 |
| CN | 101477683 A | | 7/2009 |
| CN | 101664316 A | | 3/2010 |
| CN | 103218793 A | | 7/2013 |
| CN | 204204383 A | | 3/2015 |
| CN | 104574327 A | | 4/2015 |
| CN | 104574361 A | | 4/2015 |
| WO | WO2014194160 A1 | | 12/2014 |

OTHER PUBLICATIONS

Tom Kimpe et al.; 4.5: Important Differences Between Medical Displays and Normal Desktop Displays and Underlying Reasons; Americas Display Eng. Appl. Conf.(ADEAC), 2006; Retrieved from the Internet on Apr. 28, 2019: http://citeseerx.ist.psu.edu/viewdoc/download7doM0.1.1,558.3128&rep=rep1&type=pdf (Year: 2006).*
Web; Contrast Stretching (Image Processing); Jan. 19, 2013; Retrieved from the Internet on Apr. 29, 2019: http://web.archive.org/web/20130119021708/http://what-when-how.com/embedded-image-processing-on-the-tms320c6000-dsp/contrast-stretching-image-processing/ (Year: 2013).*
CN-101477683-A (Machine Translation on Apr. 28, 2019) (Year: 2009).*
CN-101393010-A (Machine Translation on Apr. 28, 2019) (Year: 2009).*
International Search Report PCT/CN2015/092253, International Filing Date Oct. 20, 2015, dated Jul. 1, 2016.

* cited by examiner

DISPLAY GRAY SCALE CURVE CORRECTION SYSTEM AND METHOD FOR MOLYBDENUM TARGET MAMMOGRAPHY

FIELD OF THE INVENTION

The present invention relates to a display gray scale curve correction system and method for molybdenum target mammography, and more particularly to a display gray-scale curve correction system and method by using an upper computer and a display for gray-scale curve correction processing according to the image features of a breast mammography itself so as to realize the display effect enhancement of the mammography image.

BACKGROUND OF THE INVENTION

With the continuous development of the medical industry, the diagnosticians has raised a higher requirement on the display effect of a medical image so as to improve the efficiency and accuracy of medical diagnosis, and the application of professional medical monitor has become more and more popular. Different from the normal displays, medical displays usually apply DICOM correction to make the output grayscale levels comply with the Grayscale Standard Display Function (GSDF) and thus the diagnosticians be capable of distinguishing each grayscale level.

However, DICOM correction only takes into account the human eye's ability to recognize the change of the grayscale level, and not the characteristics of the image to be displayed. So for medical images in certain fields, such as a mammography X-ray image, the DICOM curve can not be used to enhance the display of the tissue site that might have a lesion.

The method of the present application makes improvements to DICOM curve, and by analyzing a mammography X-ray image and optimizing gray-scale curve according to the characteristics of the mammography X-ray image, the grayscale level of the lesion possibly present in the mammography X-ray image is highlighted, potential lesions are easier to be identified, and the diagnosis efficiency and accuracy of lesions for the doctor are further improved. In addition, the gray-scale curve correction operation of the method is conducted in FPGA loaded by the display board in real time, and it does not occupy the computing resources of the upper computer to correct extremely high resolution mammography X-ray image and make the system run smoothly.

SUMMARY OF THE INVENTION

In view of the disadvantages of the existing professional medical display technology, the present invention proposes a display gray scale curve correction system and method for molybdenum target mammography.

To achieve above purpose, the present application provides a first embodiment: a key module for providing signal input, an ARM module for receiving triggered instructions from the key module, an upper computer connected with the ARM module in two directions, an FPGA module connected with the outputs of the ARM module and the upper computer, and a display panel connected with the output of the FPGA module,
wherein the upper computer firstly captures the currently displayed mammography, then analyzes the image features, calculates the optimized gray scale correction curve, and the ARM module writes the gray scale correction curve into the FPGA module through a serial communication protocol;
the FPGA module performs grayscale mapping twice for pixel values of the input image, according to the received grayscale correction curve and the standard DICOM correction, and enhances the display of the mammography image, wherein the serial communication protocol is preferably SPI or I$^2$C protocol.

Based on above technical solution, further embodiments are provided as follows:

In the analysis of the image features by the upper computer, two kinds of inefficient information: "low gray-scale pixels of the transition zone between the skin and the background of the mammography image" and "a certain percentage of the maximum brightness pixels" are ignored, and the grayscale stretching operation is performed.

According to different types of mammary gland, the upper computer designs two optimization schemes respectively, and in the process of the gray scale transformation correction, enhances the high grayscale gland tissue and low grayscale fibrous trabecular tissue respectively in the displayed image.

The upper computer locates the gray-scale calibration curve by inserting feature points, and then obtains the entire curve by piecewise interpolation of feature points, wherein the piecewise interpolation algorithm executed by the upper computer uses both linear interpolation and three order (cubic) Hermite interpolation algorithm.

The FPGA module has more than two look-up tables, and carries out two grayscale mappings to perform grayscale correction on a target image grayscale, by using a curve obtained by the upper computer piecewise interpolation algorithm and the DICOM curve respectively.

According to the second embodiment, the present invention proposes a display gray scale curve correction method for molybdenum target mammography, comprising:
S1: an ARM module sends a trigger instruction to an upper computer when it detects a triggering instruction from a key module;
S2: the upper computer captures a currently displayed breast image, analyzes the image features, calculates the optimized gray-scale correction curve, and transmits the curve to the ARM module, when it receives the trigger instruction;
S3: the ARM module writes the correction curve into an FPGA module through a relevant protocol;
S4: according to the received optimization curve and a standard DICOM curve, the FPGA module performs two gray-level mappings on the pixel values of the input image and then outputs the corrected pixel gray-scale values to a display panel.

In Step S2, the grayscale pixel points that are irrelevant and less relevant to diagnosis in the image are ignored.

In step S2, according to the characteristics of the breast, different optimization schemes are adopted for the curve: for fat type mammary gland, the curve is designed to weaken the display effect of the high-grayscale part and enhance the texture features of the low-grayscale part; for the dense mammary gland of gland type, the curve is designed to weaken the display effect of the low grayscale part and enhance the gland organization of high grayscale parts.

In Step S2, the upper computer captures the current breast mammography X-ray images, and performs feature analysis based on the target image grayscale histogram, expressed as:

$$y=f(x), (0 \leq x \leq 2^b-1, x \in Z)$$

b represents the gray-scale bits of the display (display data width), Z represents collection of positive integers. From this gray-scale histogram, two feature points will be extracted: $P_0(x_0, 0)$ and $P_1(x_1, 2^b-1)$. $x_0$ is the maximum positive integer satisfying $f(x_1)<2 \cdot T_1$ wherein $T_1$ is defined to be the minimum value of y. $x_1$ is the maximum integer satisfying $\int_{x_1}^{2^b-1} f(x) > T_2$ wherein $T_2$ is defined to be 0.002% of the total pixels in the image.

The upper computer then calculates the coordinates of $P_2$, $P_3$ and $P_4$ based on the coordinates of $P_0$ and $P_1$. $P_2$, $P_3$ and $P_4$ come from the statistics of the grayscale curves of a large number of breast mammography images, which contains the common features of breast images.

The curve calculation of the present invention is mainly two aspects of optimization and correction:

The first aspect is to compensate for the difference in image personality caused by different shooting conditions. According to the histogram distribution of images, the grayscale distribution of the target image can make full use of all the grayscale values (entire grayscale range) of the display through grayscale stretching. In the premise of not affecting the observation effect, the gray-scale pixels in the image irrelevant and less relevant to the diagnosis are also ignored: the pixels in the transition zone between the breast skin and the background are ignored; and 0.002% of pixel points with the maximum brightness of the image are ignored. This treatment is mainly to ignore the inefficient information in a part of the breast images and increase the range of gray scales that can be used in the region of interest.

The second aspect is to use different optimizations for the curve according to the characteristics of the mammary gland (Bi-RADS-defined mammary gland morphology). For fat-type mammary glands (A/B type in Bi-RADS), the designed curve optimization scheme weakens the display of high grayscale, while emphasizing the texture features of low grayscale. For the dense mammary gland of gland type (C-D type in Bi-RADS), the curve optimization is designed to weaken the display of low-grayscale part and more emphasize on the gland organization of high grayscale parts, in order to help doctors more easy to find the lumps and nodules that may be concealed by dense glandular tissue.

Compared with the prior art, the present invention has the following advantages:

1) Compared with the standard DICOM calibration curve, the features of the mammography X-ray image are included in the scope of the optimization, which can highlight the possible parts of the lesion.

2) The process of curve optimization not only takes into account the statistical characteristics shared by breast mammography images, but also compensates for the individual differences caused by differences in shooting conditions.

3) Two built-in optimized curves are suitable for A/B type mammary glands (less glands, more fat) and C/D type mammary glands (large number of glands, dense) specified in Bi-RADS respectively.

4) it is convenient to switch the normal DICOM curve and the breast optimization curve provided by the method of the present invention through the button of the display.

5) The display on-board FPGA is used for grayscale mapping operation, which does not occupy the upper computer resources to ensure smooth operation.

THE MODE OF CARRYING OUT THE INVENTION

Figure 1:
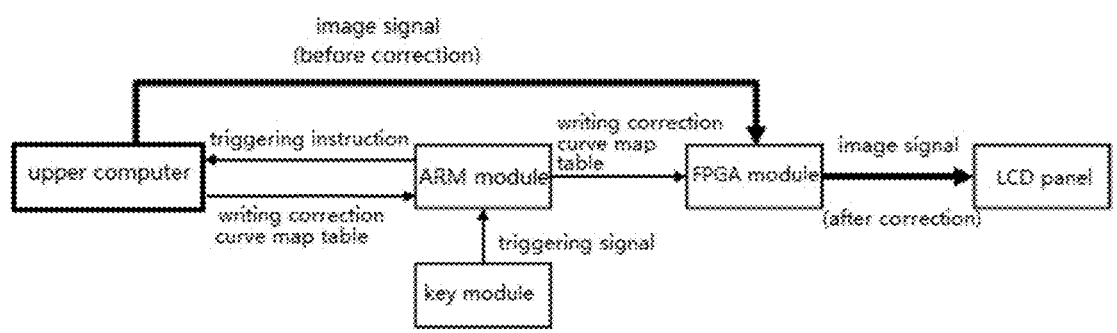
FIG. 1 shows a hardware frame diagram of the present invention.
Figure 2:
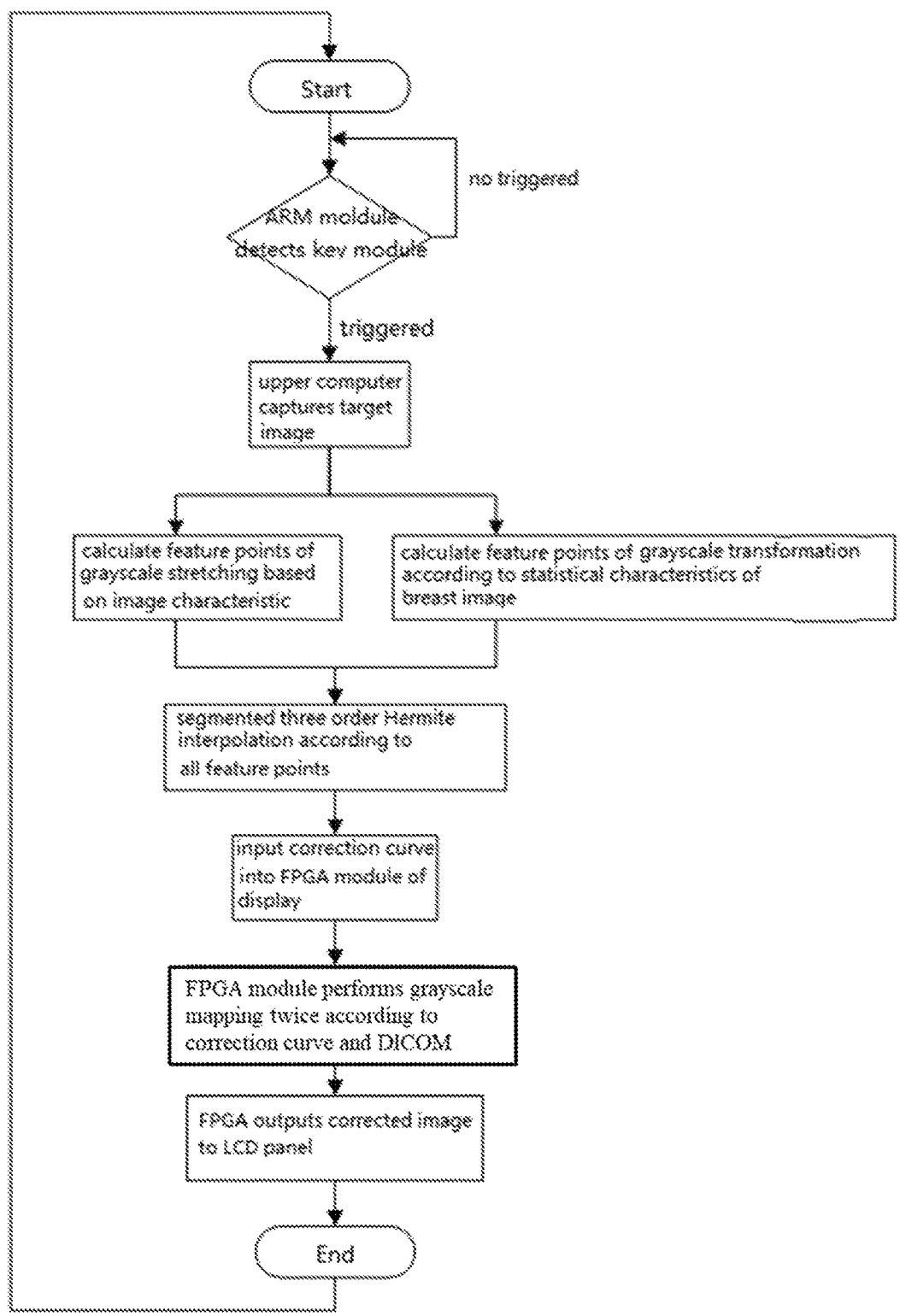
FIG. 2 shows a workflow chart of the present invention.
Figure 3:
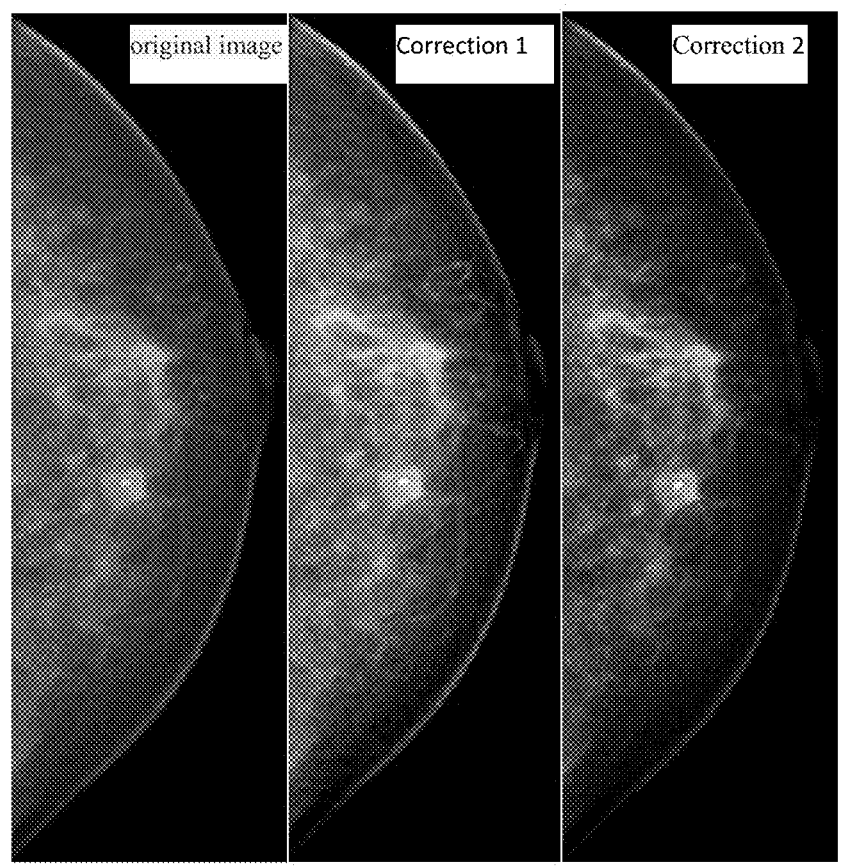
FIG. 3 shows an implementation effect diagram of the present invention, wherein original image corresponds to no correction, correction 1 corresponds to the first optimization and correction 2 corresponds to the second optimization as described below.

As shown in FIGS. 1-3, the present invention provides an embodiment of a display gray scale curve correction system for molybdenum target mammography, which comprises: a key module for providing signal input, an ARM module for receiving triggered instructions from the key module, an upper computer connected with the ARM module in two directions, an FPGA module connected with the outputs of the ARM module and the upper computer, and a display panel connected with the output of the FPGA module, wherein the upper computer firstly captures the currently displayed mammography, then analyzes the image features, calculates the optimized gray scale correction curve, and the ARM module writes the gray scale correction curve into the FPGA module through a serial communication protocol; the FPGA module performs grayscale mapping twice for pixel values of the input image, according to the received gray-scale correction curve and the standard DICOM correction, and enhances the display of the mammography image, wherein the serial communication protocol is preferably SPI or I$^2$C protocol.

According to the second embodiment, the present invention provides a display gray scale curve correction method for molybdenum target mammography, comprising:

S1: an ARM module sends a trigger instruction to an upper computer when it detects a triggering instruction from a key module;

S2: the upper computer captures a currently displayed breast image, analyzes the image features, calculates the optimized gray-scale correction curve, and transmits the curve to the ARM module, when it receives the trigger instruction;

S3: the ARM module writes the correction curve into an FPGA module through a relevant protocol;

S4: according to the received optimization curve and a standard DICOM curve, the FPGA module performs two gray-level mappings on the pixel values of the input image and then outputs the corrected pixel gray-scale values to a display panel.

When the ARM module of the display detects the operation of the key module, if the triggering action for curve correction is detected, the ARM module sends a trigger instruction to the upper computer. The upper computer captures the current breast mammography X-ray images, and performs feature analysis, primarily based on the target image grayscale histogram, expressed as:

$$y=f(x), (0 \leq x \leq 2^b-1, x \in Z)$$

b represents the gray-scale bits of the display (display data width), Z represents collection of positive integers. From this gray-scale histogram, two feature points will be extracted: $P_0(x_0, 0)$ and $P_1(x_1, 2^b-1)$, and the two feature points are primarily used to compensate the image difference resulting from the X-ray shooting parameters.

$x_0$ is the maximum positive integer satisfying $f(x_0)<kT_1$ which represents the boundary point of skin tissue and breast tissue. $T_1$ is defined to be the smallest minimum value of y, in fact represents the approximate grayscale value of skin tissue; k is the threshold coefficient that distinguishes the skin tissue from other tissues. According to repeated tests on a large number of breast pictures, the result shows that the segmentation effect is better when k is 2, which is the empirical value.

$x_1$ is the maximum integer satisfying $\int_{x_1}^{2^b-1} f(x) > T_2$, and represents the boundary point of the maximum grayscale pixels in the screen, and $T_2$ is defined as the percentage of the total number of pixels in the screen. After repeated tests on a large number of breast images, the optimization results are better when the value of $T_2$ is 0.002% which is the empirical value.

The upper computer then calculates the coordinates of $P_2$, $P_3$ and $P_4$ based on the coordinates of $P_0$ and $P_1$. $P_2$, $P_3$ and $P_4$ come from the statistics of the grayscale curves of a large number of breast mammography images, which contains the common features of breast images.

The present invention provides two kind of optimization algorithms. The two optimizations share the coordinates of $P_0$ and $P_1$, but the coordinates of $P_2$, $P_3$ and $P_4$ are different.

The first optimization (designed for type A/B breast specified in Bi-RADS) (see correction 1 in FIG. 3):

$$\begin{cases} P_2 \lfloor x_1 + 0.1484*(x_5-x_1), 0.2148*(2^b-1) \rfloor \\ P_3 \lfloor x_1 + 0.2656*(x_5-x_1), 0.3398*(2^b-1) \rfloor \\ P_4 \lfloor x_1 + 0.5625*(x_5-x_1), 0.6016*(2^b-1) \rfloor \end{cases}$$

The second optimization (designed for type C/D breast specified in Bi-RADS) (see correction 2 in FIG. 3):

$$\begin{cases} P_2 \lfloor x_1 + 0.1523*(x_5-x_1), 0.1250*(2^b-1) \rfloor \\ P_3 \lfloor x_1 + 0.2734*(x_5-x_1), 0.2070*(2^b-1) \rfloor \\ P_4 \lfloor x_1 + 0.4766*(x_5-x_1), 0.3945*(2^b-1) \rfloor \end{cases}$$

Besides these 5 featured points, another two featured points with fixed coordinates are added: $P_5(0, 0)$ and $P_6(2^b-1, 2^b-1)$. So, a total of seven feature points on the curve are obtained. A complete gray-scale correction curve $C_{(x)}$ may be obtained by the interpolation algorithm, wherein interpolation is carried out only in the definition domain of f(x). The interpolation algorithm is performed in segments, using linear interpolation between $P_5$ and $P_0$ as well as between $P_1$ and $P_6$, and the segmented three order Hermite interpolation algorithm between the other feature points.

The calculated curve C(x) is transmitted to the FPGA module through the ARM module. Two grayscale mapping operations are performed in the FPGA module through two look-up tables (FUTs), the first grayscale mapping according to C(x), and the second grayscale mapping according to the GSDF function curve specified in the DICOM standard, the final value obtained by the mapping is used to drive the LCD panel to complete the image display.

The method of the present application makes improvements to DICOM curve, by taking into account the characteristics of the breast image itself, the grayscale level of the lesion possibly present in the mammography X-ray image is highlighted, and potential lesions are easier to be identified. The adjustment of the curve is mainly aimed at two aspects. One is to compensate for the difference in images caused by different shooting conditions. The other is the tissue grayscale distribution of the lesion possibly present in the mammography X-ray image, and two kinds of optimization algorithms is designed for different breast types. The present invention has the following advantages:

1. Compared with the standard DICOM calibration curve, the features of the mammography X-ray image are included in the scope of the optimization, which can highlight the possible parts of the lesion.

2. The process of curve optimization not only takes into account the statistical characteristics shared by breast mammography images, but also compensates for the individual differences caused by differences in shooting conditions.

3. Two built-in optimized curves are suitable for A/B type mammary glands (less glands, more fat) and C/D type mammary glands (large number of glands, dense) specified in Bi-RADS respectively.

4. It is convenient to switch the normal DICOM curve and the breast optimization curve provided by the method of the present invention through the button of the display.

5. The display on-board FPGA is used for grayscale mapping operation, which does not occupy the upper computer resources to ensure smooth operation.

It will be understood by those skilled in the art that, the above embodiments are only for illustrating the technical idea and features of the present invention, and are intended to enable those skilled in the art to understand and implement the contents of the present invention, and are not intended to limit the protection scope of the present invention. Any equivalent modifications made without departing from the spirit of the present invention shall fall within the protection scope of the present invention.

The invention claimed is:

1. A display gray scale curve correction system for molybdenum target mammography, comprising:
    a key module for providing signal input, an Acorn RISC Machines (ARM) module for receiving triggered instructions from the key module, an upper computer connected with the ARM module in two directions, a Field Programming Gate Array (FPGA) module connected with the outputs of the ARM module and the upper computer, and a display panel connected with the output of the FPGA module, wherein the upper computer firstly captures the currently displayed mammography, then analyzes the image features, calculates an optimized gray scale correction curve, and the ARM module writes the gray scale correction curve into the FPGA module through a serial communication protocol, and wherein an analysis and a calculation are performed by a processor in the upper computer;
    the FPGA module performs grayscale mapping twice for pixel values of the input image, according to the received grayscale correction curve and a standard Digital Imaging and Communications in Medicine (DICOM) correction, and enhances the display of the mammography image, wherein the serial communication protocol is preferably Serial Peripheral Interface (SPI) or Inter-Integrated Circuit (I2C) protocol, wherein, in the analysis of the image features by the upper computer, two kinds of inefficient information:
    (i) low gray-scale pixels of the transition zone between the skin and the background of the mammography image and (ii) a certain percentage of the maximum brightness pixels are ignored, and a grayscale stretching operation is performed; and
    wherein according to different types of mammary gland, the upper computer designs two optimization schemes respectively, and in a process of the gray scale transformation correction, enhances the high grayscale gland tissue and low grayscale fibrous trabecular tissue respectively in the displayed image.

2. The display gray scale curve correction system as claimed in claim 1, wherein the upper computer locates the gray-scale calibration curve by inserting feature points, and then obtains the entire curve by piecewise interpolation of feature points,
wherein a piecewise interpolation algorithm executed by the upper computer uses both the linear interpolation and three order Hermite interpolation algorithm.

3. The display gray scale curve correction system as claimed in claim 2, wherein the FPGA module has more than two look-up tables, and carries out two grayscale mappings to perform grayscale correction on a target image grayscale, by using a curve obtained by the upper computer piecewise interpolation algorithm and a DICOM curve respectively.

4. A display gray scale curve correction method for molybdenum target mammography, comprising:
S1: an Acorn RISC Machines (ARM) module sends a trigger instruction to an upper computer when it detects a triggering instruction from a key module;
S2: the upper computer captures a currently displayed breast image, analyzes the image features, calculates an optimized gray-scale correction curve, and transmits the curve to the ARM module, when it receives the trigger instruction, wherein an analysis and a calculation are performed by a processor in the upper computer;
S3: the ARM module writes the correction curve into a Field Programming Gate Array (FPGA) module through a relevant protocol; and
S4: according to the received optimization curve and a standard Digital Imaging and Communications in Medicine (DICOM) curve, the FPGA module performs two gray-level mappings on the pixel values of the input image and then outputs the corrected pixel gray-scale values to a display panel;
wherein in step S2, according to the characteristics of the breast, different optimization schemes are adopted for the curve:
for fat type mammary gland, the curve is designed to weaken the display effect of the high-grayscale part and enhance the texture features of the low-grayscale part, and
for the dense mammary gland of gland type, the curve is designed to weaken the display effect of the low grayscale part and enhance the gland organization of high grayscale parts.

5. The display gray scale curve correction method as claimed in claim 4, wherein in Step S2, the grayscale pixel points that are irrelevant and less relevant to diagnosis in the image in step S2 are ignored.

6. The display gray scale curve correction method as claimed in claim 4, wherein in Step S2, the upper computer captures the current breast mammography X-ray images, and performs feature analysis based on the target image grayscale histogram, expressed as:

$$y=f(x), (0 \leq x \leq 2^b-1, x \in Z)$$

b represents the gray-scale bits of the display (display data width), Z represents collection of positive integers, and two feature points will be extracted from this gray-scale histogram: $P_0(x_0, 0)$ and $P_1(x_1, 2^b-1)$;

$x_0$ is the maximum positive integer satisfying $f(x_0)<kT_1$ which represents the boundary point of skin tissue and breast tissue, wherein $T_1$ is defined to be the minimum value of y;

$x_1$ is the maximum integer satisfying $\int_{x_1}^{2^b-1} f(x) > T_2$ which represents the boundary point of the maximum grayscale pixels in the screen, wherein $T_2$ is defined as the percentage of the total number of pixels in the screen;

the upper computer then calculates the coordinates of $P_2$, $P_3$ and $P_4$ based on the coordinates of $P_0$ and $P_1$, $P_2$, $P_3$ and $P_4$ come from the statistics of the grayscale curves of a large number of breast mammography images, which contains the common features of breast images.

* * * * *